March 5, 1940. N. GRILLO Plant Pat. 367
ROSE
Filed Jan. 23, 1939
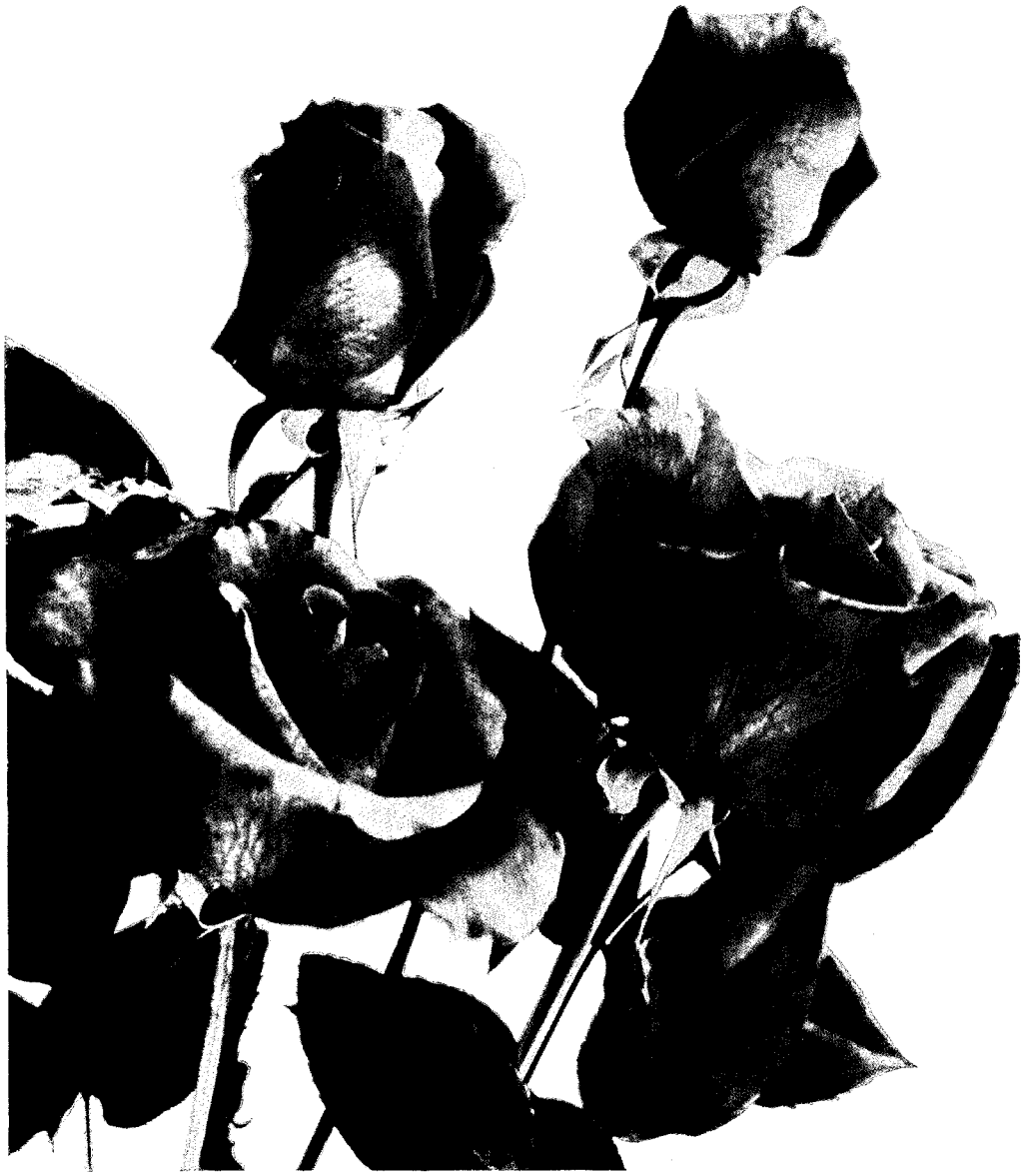
INVENTOR
Nicholas Grillo
By Orville M Kile
Plant Patent Agent Patented Mar. 5, 1940

Plant Pat. 367

UNITED STATES PATENT OFFICE

367

ROSE

Nicholas Grillo, Milldale, Conn.

Application January 23, 1939, Serial No. 252,499

1 Claim. (Cl. 47—61)

My new discovery relates to a new and distinct variety of hybrid tea roses and was originated as a sport of Better Times which is the subject of Plant Patent No. 23. I discovered this new sport as a branch on a plant of Better Times growing in my greenhouse.

My new variety possesses many of the characteristics of its parent but differs from it in several important respects. The most outstanding differences lie in the darker shade of the flower of this new variety, its more prolific growth, its stronger stems, and its better keeping qualities. I have asexually reproduced this variety and have found the qualities above referred to have become firmly fixed.

The accompanying illustration shows four views of specimens of this variety in various stages of opening. Although the color is approximately as the artist has depicted it, there is much more brilliance than can be shown.

Color plate references are to Ridgway's Color Standards and Nomeclature. Where no reference is given, the ordinary dictionary definition is intended.

Following is a detailed description of my new variety.

*The plant*

Growth habits:

Upright bush; very vigorous; produces a great many flowers and long, strong stems.

Foliage:

Abundant.

*Leaflets.*—Three to five, occasionally seven. Size—medium, terminal leaflet averages 3 inches by 1½ inches. Color—Dark Dull Yellow Green (Plate XXXII). Has a decided tinge of Hydrangea Red (Plate XXVII) on the under surface and around the edges of the new foliage. Shape—oval with acuminate apex. Texture—heavy. Edge—sharply and evenly serrated.

*Rachis.*—Grooved above; has several spines on under side.

*Stipules.*—Medium; clinging; have long sharp points which in many instances are curved.

*Stems.*—Very strong; long; Cerro Green (Plate V).

*Thorns.*—None on peduncle but many toward base of stem; Mignonette Green (Plate XXXI), usually tinged with pink; downward pointing.

*Sepals.*—Larger and longer than those of its parent. Of varying lengths and two of the five are inclined to be foliaceous. Curl backward.

*The flower*

The bud:

*Shape.*—Long; pointed.

*Color.*—Slightly darker than the bloom, being almost Amaranth Purple (Plate XII).

*Opening.*—Gradual and perfect.

The bloom:

*Size.*—Medium to large. In warm weather 4 to 4½ inches across; in cooler weather 4½ to 5 inches across.

*Borne.*—Singly.

*Form.*—High centered at first. Much later it spreads into rather ragged form. Even when the outer petals are wide open, a few of the central petals form a cone for some time before finally opening to reveal the stamens. When the flower is completely opened the outer petals tend to quill.

*Color.*—The color of the blossoms of this variety is not found in Ridgway's Color Standards and Nomenclature but falls between the shades of Tyrian Rose and Amaranth Purple (Plate XII), is almost uniformly distributed, and does not change for several days after cutting. There is a brilliance about the color which cannot be adequately shown in the illustrations, and in cooler weather the flower is somewhat darker and more velvety. One notable feature of this rose is the fact that no light area appears at the base of the petals on their outer surface. In fact, the base is slightly darker in shade than the rest of the petal. On the inner surface of the petals there appears a lighter portion at the base, and the small aiglet is white. When the flower fully opens it seems to become lighter because a greater portion of the inside surface of the petals is visible.

*Petalage.*—Under normal conditions in the month of September, there are 42 or 43 petals including 6 or 8 petaloids. Petals:—Appearance—velvety on upper surface. Texture—heavy. Shape—broadly obovate. Size—the outer pedals are much larger than the inner ones. Outer petals measure 1¾ inches to 2 inches wide by approximately the same in vertical measurement. Petals gradually diminish in size advancing toward the center.

*Fragrance.*—Definite and lasting, but not too strong to be pleasing.

*Behavior.*—Clinging.

*Longevity.*—Excellent, surpassing its parent in this respect. No apparent change in color occurs as the flower ages, until after several days (usually about a week).

*Reproductive organs*

Pistils:

Many; uneven lengths with longest in center; styles creamy white, merging into the Spinel Red (Plate XXVI) of the stigmas which are tipped with a dot of yellowish white.

Stamens:

Few; surround pistils in uneven lengths; filaments Rose Red (Plate XII), topped with anthers which are Light Orange Yellow (Plate III) above and Spinel Red (Plate XXVI) on the under side.

*Comparison with Plant Patent #295*

The rose known to me which is the most nearly like my new rose is the subject of Plant Patent No. 295. However, it differs from that rose in several important respects, most notable of which are as follows:

1. The color of my new variety is more uniformly spread over the entire petal, there being no light portion at the base of the petal on its outer surface. The subject of Plant Patent #295 has a large light area at the base of the petals both inside and outside.
2. My new variety has a greater number of petals than #295.
3. The outer petals of my new variety have a slight tendency to quill when the flower is fully opened, and this is not the case with #295.
4. The outer petals of my variety are not so large as those of #295.
5. My new variety has slightly more brilliance to its color. The two varieties are distinguishable in color although they are in the same color range.

Having thus disclosed my discovery, I claim:

The new and distinct variety of hybrid tea rose as shown and described, characterized particularly by its strong stems; its vigorous growth; and its prolific production of flowers having excellent keeping qualities, lasting fragrance, and distinctive unfading and evenly distributed color between Tyrian Rose and Amaranth Purple.

NICHOLAS GRILLO.